United States Patent [19]

Shinoda

[11] Patent Number: 5,414,110

[45] Date of Patent: May 9, 1995

[54] RU-SN HETERO-POLYNUCLEAR COMPLEX AND PROCESS FOR PRODUCING ACETIC ACID OR METHYL ACETATE BY USING THE SAME

[75] Inventor: Sumio Shinoda, Tokyo, Japan

[73] Assignee: Daicel Chemical Industries, Ltd., Osaka, Japan

[21] Appl. No.: 211,050

[22] PCT Filed: Sep. 9, 1993

[86] PCT No.: PCT/JP93/01282

§ 371 Date: Mar. 10, 1994

§ 102(e) Date: Mar. 10, 1994

[87] PCT Pub. No.: WO94/05420

PCT Pub. Date: Mar. 17, 1994

[30] Foreign Application Priority Data

Sep. 10, 1992 [JP] Japan ................... 4-269737

[51] Int. Cl.$^6$ .................. C07C 53/08; C07C 51/16; B01J 31/16; C07B 61/00
[52] U.S. Cl. ................... 560/238; 502/261; 560/231; 560/232; 562/607
[58] Field of Search ........................ 560/238; 556/136

[56] References Cited

U.S. PATENT DOCUMENTS

| | | | |
|---|---|---|---|
| 4,626,334 | 12/1986 | Ohe et al. | 204/290 R |
| 5,214,184 | 5/1993 | Matuzaki et al. | 558/277 |
| 5,334,769 | 8/1994 | Ferrero et al. | 568/435 |

OTHER PUBLICATIONS

1 C4 37 One–Step Formation Reaction (4) of Acetic Acid (Methyl Acetate) with Methanol Used as the Sole Source . . . , Institute of Industrial Science, Univ. of Tokyo, and English translation (1990).
1 C4 38 Conversion Reaction of Methanol with Supported–Ru(II)–Sn(II) Heteronuclear Cluster . . . , Institute of Industrial Science, Univ. of Tokyo, and English Translation (1990).

*Primary Examiner*—Arthur C. Prescott
*Attorney, Agent, or Firm*—Flynn, Thiel, Boutell & Tanis

[57] ABSTRACT

The present invention relates to (1) a Ru-Sn hetero-polynuclear complex as a novel catalyst which has a high catalytic activity and is useful for producing acetic acid and/or methyl acetate from methanol, and (2) a process for producing acetic acid and/or methyl acetate through a one-stage reaction starting with methanol wherein a catalyst can be used at a high concentration and the catalytic activity is maintained throughout the reaction.

27 Claims, 1 Drawing Sheet

RU-SN HETERO-POLYNUCLEAR COMPLEX AND PROCESS FOR PRODUCING ACETIC ACID OR METHYL ACETATE BY USING THE SAME

This application was filed under 35 U.S.C. 371, based on Internal Application No. PCT/JP93/01282 filed Sep. 9, 1993 with priority date Sep. 10, 1992.

FIELD OF THE INVENTION

The present invention relates to a novel Ru-Sn hetero-polynuclear complex useful as a catalyst and a process for producing acetic acid and/or methyl acetate in the presence of the complex by using methanol, methyl formate or formaldehyde as a starting material.

RELATED ART

Acetic acid has been industrially produced in a large amount by the methanol carbonylation method, i.e., so-called Monsanto's method. In this method, methanol is reacted with carbon monoxide in a liquid phase in the presence of a catalytic system containing a rhodium catalyst and an iodide.

However, it is necessary in these methods to use rhodium, which is very expensive. Further, the conditions of location of the factory are restricted because it is necessary to obtain carbon monoxide of a high purity. Furthermore, there is a problem that methyl iodide, which is used as an iodide, corrodes the apparatus. In addition, since the above-mentioned reaction is usually effected in a liquid phase system containing water, the recovery of the acetic acid thus formed requires much energy.

Meanwhile, there has been proposed the use of an Ru-Sn heteronuclear cluster (a polynuclear compound) containing an anion comprising $[Ru(SnCl_3)_5L]^{3-}$ (wherein L represents a ligand) as a catalyst for producing acetic acid and methyl acetate from methanol through a one-stage reaction in a liquid phase [Sumio Shinoda and Tetsu Yamakawa, "One-step Formation of Methyl Acetate with Methanol used as the Sole Source and Catalysis by $Ru^{II}$-$Sn^{II}$ Cluster Complexes", J. Chem. Soc., Chem. Commun., p.p. 1511–1512 (1990)].

However, the above-mentioned heteronuclear cluster has a solubility in methanol as small as about 0.05 mM. In addition, since the above heteronuclear cluster is an anionic complex, the solubility of the above heteronuclear cluster is smaller not only in the acetic acid formed but also in common organic solvents. Thus, it is impossible to elevate the concentration of the catalyst, and therefore the reaction rate also can not be enhanced. Furthermore, it is sometimes observed that formaldehyde is formed by the dehydrogenation of methanol and the metal contained in the catalyst is reduced and precipitated by the formaldehyde, which causes the deactivation of the catalyst within a short period of time. In particular, the catalyst is liable to be deactivated when reacted at a high temperature.

On the other hand, there have also been known $CpRu(PR_3)_2L$ and $CpRu\{P(OR_3)\}_2^L$ (wherein Cp represents a cyclopentadienyl group which may be substituted; R represents an alkyl group, a cycloalkyl group, an aryl group or an aralkyl group; and L represents a specific monovalent anion ligand) as a complex containing Ru [S. G. Davies, et al., Adv. Organomet. Chem., 30, 1 (1990)]. These complexes are deemed to be highly stable in structure and, therefore, there is a possibility that these Complexes can be used as a catalyst in a reaction at a relatively high temperature.

Further, a method for synthesizing $CpRu(PPh_3)_2Cl$, which is one of these complexes, is described in M. I. Bruce, et al., Inorg. Synth., 28, 270 (1990) and a method for synthesizing $CpRu(PPh_3)_2SnCl_3$, which is one of these complexes, is described in T. Blackmore, et al., J. Chem. Soc. A, 2376 (1971).

However, there has been clarified so far no catalyst which is useful in the production of acetic acid and/or methyl acetate from, for example, methanol and free from any of the above-mentioned problems.

Accordingly, it is an object of the present invention to provide a novel catalyst which has a high catalytic activity and is useful for producing acetic acid and/or methyl acetate from methanol.

It is another object of the present invention to provide a process for producing acetic acid and/or methyl acetate through a one-stage reaction starting with methanol wherein a catalyst can be used at a high concentration and the catalytic activity is maintained throughout the reaction.

It is another object of the present invention to provide a process for producing acetic acid and/or methyl acetate in the presence of a highly active catalyst at a high reaction rate.

DISCLOSURE OF THE INVENTION

The present inventor has extensively studied to attain the above-mentioned objects. As a result, he has developed a novel Ru-Sn hetero-polynuclear complex and, at the same time found that the above-mentioned objects can be achieved by reacting methanol, methyl formate or formaldehyde with the use of this catalyst. The present invention has been accomplished on the basis of these findings.

Thus, the present invention relates a catalyst represented by the following general formula (10):

$$Ru(SnY_3)_m(L)_n \qquad (10)$$

[wherein Y represents a halogen atom, an alkyl group, a cycloalkyl group, an aryl group, an aralkyl group or an alkoxyl group, L represents a ligand, m is an integer of 1 to 6, n is an integer of 0 to 5 and m+n is an integer of 1 to 6].

As the above catalyst, one represented by the general formula (1), wherein m is 1 or 2, n is an integer of 1 to 5 and m+n is 5 or 6, or another one represented by the general formula (1), wherein Y is a halogen atom, particularly a fluorine atom or a chlorine atom, is preferable.

Further, the catalyst represented by the general formula (10) may be one represented by the following general formula (1):

$$Ru(SnY_3)_m(L)_n \qquad (1)$$

[wherein Y represents a halogen atom, an alkyl group, a cycloalkyl group, an aryl group, an aralkyl group or an alkoxyl group, L represents a ligand, m is an integer of 1 to 6, n is an integer of 0 to 5 and m+n is an integer of 1 to 6, with the proviso that the general formula (1) does not represent $CpRu(SnCl_3)(L^a)_2$ {wherein Cp represents a cyclopentadienyl group, $L^a$ represents $PPh_3$, $AsPh_3$ or ½{1,2-bis(diphenylphosphino)propane} (wherein Ph represents a phenyl group)}].

As the above catalyst, one represented by the general formula (10), wherein L is at least one ligand selected from the group consisting of a halogen atom, a hydrogen atom, a coordinative carbon-containing ligand, a coordinative nitrogen-containing ligand, a coordinative oxygen-containing ligand, a coordinative phosphorus-containing ligand, a coordinative sulfur-containing ligand and a coordinative arsenic-containing ligand, or at least one ligand selected from the group consisting of a halogen atom, a hydrogen atom, a coordinative carbon-containing ligand (exclusive CO), a coordinative nitrogen-containing ligand, a coordinative oxygen-containing ligand (exclusive CO), a coordinative phosphorus-containing ligand, a coordinative sulfur-containing ligand and a coordinative arsenic-containing ligand is also preferably used.

Particularly, one represented by the general formula (10), wherein L is at least one ligand selected from the group consisting of a halogen atom, $PR^a_3$ (wherein $R^a$ represents an alkyl group, a cycloalkyl group, an aryl group, an aralkyl group, an alkoxyl group, an aryloxy group or an arylalkoxyl group), $P(OR^b)_3$ (wherein $R^b$ represents an alkyl group, a cycloalkyl group, an aryl group or an aralkyl group), ½{bis(diphenylphosphino)alkane} and a monovalent cyclic dienyl group is preferable as the above catalyst.

Further, as the above catalyst, one represented by the following general formula (2) is preferable:

$$RuX_c\{P(OR^b)_3\}_d(SnY^a_3)_m \qquad (2)$$

[wherein X and $Y^a$ is the same or different from each other and each represents a halogen atom, $R^b$ represents an alkyl group, a cycloalkyl group, an aryl group or an aralkyl group, c is 0 or 1, m is 1 or 2, c+m is 2, d is 3 when c is 0 and d is 4 when c is 1].

Furthermore, as the above catalyst, one represented by the following general formulas (30), (40) or (50) is preferable:

$$ZRu\{P(OR^b)_3\}_2(SnY_3) \qquad (30)$$

[wherein Z represents a monovalent cyclic dienyl group, Y represents a halogen atom, an alkyl group, a cycloalkyl group, an aryl group, an aralkyl group or an alkoxyl group, and $R^b$ represents an alkyl group, a cycloalkyl group, an aryl group or an aralkyl group], $$ZRu(dppa)(SnY_3) \qquad (40)$$

[wherein Z represents a monovalent cyclic dienyl group, Y represents a halogen atom, an alkyl group, a cycloalkyl group, an aryl group, an aralkyl group or an alkoxyl group, and dppa represents a bid(diphenylphosphino)alkane], $$ZRu(PPh_3)_2(SnY_3) \qquad (50)$$

[wherein Z represents a monovalent cyclic dienyl group, Y represents a halogen atom, an alkyl group, a cycloalkyl group, an aryl group, an aralkyl group or an alkoxyl group, and Ph represents a phenyl group].

As the above catalyst, one represented by the following general formulas (30), (4) or (5) is preferable:

$$ZRu\{((OR^b)_3\}_2(SnY_3) \qquad (30)$$

[wherein Z represents a monovalent cyclic dienyl group, Y represents a halogen atom, an alkyl group, a cycloalkyl group, an aryl group, an aralkyl group or an alkoxyl group, and $R^b$ represents an alkyl group, a cycloalkyl group, an aryl group or an aralkyl group], $$ZRu(dppa)(SnY_3) \qquad (4)$$

[wherein Z represents a monovalent cyclic dienyl group, Y represents a halogen atom, an alkyl group, a cycloalkyl group, an aryl group, an aralkyl group or an alkoxyl group, and dppa represents a bis(diphenylphosphino)alkane, with the proviso that the general formula (4) does not represent $CpRu(1,2\text{-dppp})(SnCl_3)$ {wherein Cp represents a cyclopentadienyl group and 1,2-dppp represents 1,2-bis(diphenylphosphino)propane}], $$ZRu(PPh_3)_2(SnY_3) \qquad (5)$$

[wherein Z represents a monovalent cyclic dienyl group, Y represents a halogen atom, an alkyl group, a cycloalkyl group, an aryl group, an aralkyl group or an alkoxyl group, and Ph represents a phenyl group, with the proviso that the general formula (5) does not represent $CpRu(PPh_3)_2(SnCl_3)$ [wherein Cp represents a cyclopentadienyl group and Ph represents a phenyl group}].

As the above catalyst, one represented by the general formulas (30), (40), (50), (4) or (5) wherein Z represents a cyclopentadienyl group is most preferable.

Further, the present invention relates a process for producing acetic acid and/or methyl acetate by using at least one compound selected from the group consisting of methanol, methyl formate and formaldehyde as a starting material and effecting a reaction in the presence of the catalyst according to the present invention described above.

The term "formaldehyde" as used in this specification involves formaldehyde polymers which are equivalent thereto, such as paraformaldehyde.

Scope and the application of the present invention will become apparent from the detailed description given hereinafter. However, it should be understood that the detailed description and examples, while indicating preferred embodiments of the invention, are given by way of illustration only, since various changes and modifications within the spirit and scope of the invention will become apparent to those skilled in the art from this detailed description.

Though the present invention will be described in detail hereinafter, the scope of the present invention is not restricted by the following description.

The catalyst according to the present invention is the Ru-Sn hetero-polynuclear complex represented by the following general formula (10):

$$Ru(SnY_3)_m(L)_n \qquad (10)$$

[wherein Y represents a halogen atom, an alkyl group, a cycloalkyl group, an aryl group, an aralkyl group or an alkoxyl group, L represents a ligand, m is an integer of 1 to 6, n is an integer of 0 to 5 and m+n is an integer of 1 to 6].

As the above catalyst, one represented by the general formula (10), wherein m is 1 or 2, n is an integer of 1 to 5 and m+n is 5 or 6 is preferable.

As the above catalyst, one represented by the general formula (1) wherein m is 1 or 2, n is an integer of 1 to 5 and m+n is 5 or 6 is preferable.

Further, the catalyst represented by the general formula (10) may be one represented by the following general formula (1):

$$Ru(SnY_3)_m(L)_n \qquad (1)$$

[wherein Y represents a halogen atom, an alkyl group, a cycloalkyl group, an aryl group, an aralkyl group or an alkoxyl group, L represents a ligand, m is an integer of 1 to 6, n is an integer of 0 to 5 and m+n is an integer of 1 to 6, with the proviso that the general formula (1) does not represent $CpRu(SnCl_3)(L^a)_2$ {wherein Cp represents a cyclopentadienyl group, $L^a$ represents $PPh_3$, $AsPh_3$ or $\frac{1}{2}${1,2-bis(diphenylphosphino)propane} (wherein Ph represents a phenyl group)}].

The halogen atom, which is defined as Y in the above general formulas (10) (1), includes a fluorine atoms, a chlorine atom, a bromine atom and an iodine atom. As a preferable halogen atom, a chlorine atom and a fluorine atom may be cited.

Y may be an alkyl group, a cycloalkyl group, an aryl group, an aralkyl group or an alkoxyl group.

The ligand, which is defined as L in the above general formulas (10) (1), includes a halogen atom, a hydrogen atom, a coordinative carbon-containing ligand, a coordinative nitrogen-containing ligand, a coordinative oxygen-containing ligand, a coordinative phosphorus-containing ligand, a coordinative sulfur-containing ligand and a coordinative arsenic-containing ligand.

Now the ligand will be described more definitely.

The halogen atom as the ligand is the same as that represented by Y. As a preferable halogen atom, a chlorine atom may be cited.

Examples of the "coordinative carbon-containing ligand" as used in the present invention include alkyl groups, cycloalkyl groups, aryl groups, aralkyl groups, monovalent cyclic dienyl groups such as a cyclopentadienyl group and a cyclooctadienyl group which may be substituted, olefins which may be substituted and CO.

Examples of the "coordinative nitrogen-containing ligand" as used in the present invention include $NH_3$, amines (for example, amines such as methylamine, ethylamine, dimethylamine and diethylamine, diamines such as ethylenediamine, nitrogen-containing heterocyclic compounds such as imidazole, pyridine, pyrimidine, piperidine, piperazine, morpholine and phenanthroline and nitrogen-containing aromatic compounds such as aniline) and compounds represented by RCN (wherein R represents an alkyl group, a cycloalkyl group, an aryl group, an aralkyl group or an alkoxyl group). Among these ligands, $NH_3$ is preferable.

Examples of the "coordinative oxygen-containing ligand" as used in the present inveniton include $H_2O$, alcohols including aliphatic alcohols and aromatic alcohols, ethers including aliphatic ethers and aromatic ethers, a hydroxyl ion and alkoxide ions.

Examples of the "coordinative phosphorus-containing ligand" as used in the present invention include $PR_3$ or $O=PR_3$ (wherein R represents an alkyl group, a cycloalkyl group, an aryl group, an aralkyl group or an alkoxyl group) and bis(diphenylphosphino)alkanes such as 1,2-bis(diphenylphosphino)ethane (1,2-dppe), 1,3-bis(diphenylphosphino)propane (1,3-dppp) and 1,4-bis(diphenylphosphino)butane (1,4-dppb), i.e., bidentate phosphine ligands. Since the bis(diphenylphosphino)alkanes have bidentate coordination characteristics, L represents $\frac{1}{2}${bis(diphenylphosphino)alkane}.

Examples of the "coordinative sulfur-containing ligand" as used in the present invention include compounds represented by RSR and RSH (wherein R represents an alkyl group, a cycloalkyl group, an aryl group, an aralkyl group or an alkoxyl group).

Examples of the "coordinative arsenic-containing ligand" as used in the present invention include compounds represented by $AsR_3$ or $O=AsR_3$ (wherein R represents an alkyl group, a cycloalkyl group, an aryl group, an aralkyl group or an alkoxyl group) and bidentate arsine ligands such as 1,2-bis(diphenylarsino)ethane. Since the 1,2-bis(diphenylarsino)ethane has bidentate coordination characteristics, L represents $\frac{1}{2}${1,2-bis(diphenylarsino)ethane}.

Examples of the alkyl groups given in the description of Y and L in the above general formulas (10) and (1) include a methyl group, an ethyl group, a n-propyl group, an isopropyl group, a n-butyl group, an isobutyl group, a pentyl group and a hexyl group.

Examples of the cycloalkyl groups include a cyclopentyl group, a cyclohexyl group and a cyclooctyl group. The aryl groups include a phenyl group, a naphthyl group and the like. The aralkyl groups include a benzyl group, a phenethyl group, a benzhydryl group and the like.

Examples of the alkoxyl groups include alkoxyl groups corresponding to the above-mentioned alkyl groups, for example, a methoxy group, an ethoxy group, a n-propoxy group, an isopropoxy group, a n-butoxy group, an isobutoxy group, a pentyloxy group and a hexyloxy group.

Among these catalysts according to the present invention, a series of compounds represented by the following general formula (2) are preferable:

$$RuX_c\{P(OR^b)_3\}_d(SnY^a_3)_m \qquad (2)$$

[wherein X and $Y^a$ is the same or different from each other and each represents a halogen atom, $R^b$ represents an alkyl group, a cycloalkyl group, an aryl group or an aralkyl group, c is 0 or i, m is 1 or 2, c+m is 2, d is 3 when c is 0 and d is 4 when c is 1].

The halogen atom, alkyl group, cycloalkyl group, aryl group, aralkyl group and the like in the above formula (2) are the same as those in the general formulas (10 and (1). As a preferable substituent $R^b$ an alkyl group having 1 to 4 carbon atoms and particularly 1 to 3 carbon atoms, especially a methyl group and the like, may be cited.

Particular examples of the compound, i.e., the complex, represented by the above general formula (2) include $[RuCl(SnCl_3)\{P(OCH_3)_3\}_4]$ and $[Ru(SnCl_3)_2\{P(OCH_3)_3\}_3]$.

The complex represented by the general formula (2) can be produced by, for example, reacting a ruthenium complex represented by the formula $[RuX_2\{P(OR^b)_3\}_4]$ (wherein X and $R^b$ are each as defined above) with a tin compound such as a tin halide.

For example, a hexacoordinated complex represented by the formula $[RuX(SnY^a_3)\{P(OR^b)_3\}_4]$ (wherein X, $Y^a$ and $R^b$ are each as defined above), i.e., one represented by the general formula (2), wherein c=m=1 and d=4, can be produced by mixing a complex represented by the above-mentioned formula $[RuX_2\{P(OR^b)_3\}_4]$ (wherein X and $R^b$ are each as defined above) with a compound represented by the formula $[(PPh_4)(SnY^a_3)]$ (wherein Ph represents a phenyl group while $Y^a$ is as defined above) in an appropriate solvent at a temperature of, for example, from room temperature to the reflux temperature.

A pentacoordinated complex represented by the formula [Ru(SnY$^a$₃)₂{P(OR$^b$)₃}₃] (wherein Y$^a$ and R$^b$ are each as defined above), i.e., one represented by the general formula (2) wherein c=0, m=2 and d=3, can be produced by mixing a complex represented by the above-mentioned formula [RuX₂{P(OR$^b$)₃}₄] (wherein X and R$^b$ are each as defined above) with a compound represented by the formula SnY$^a$₂.2H₂O (wherein Y$^a$ is as defined above) in an appropriate solvent at a temperature from room temperature to the reflux temperature.

Examples of the solvent which is used in the production of the complex represented by the general formula (2) include alcohols such as methanol, ethanol, n-propanol, isopropanol, n-butanol, isobutanol, t-butanol and sec-butanol; aliphatic hydrocarbons such as hexane, heptane and octane; alicyclic hydrocarbons such as cyclohexane; aromatic hydrocarbons such as benzene, toluene and xylene; halogenated hydrocarbons such as dichloromethane, trichloromethane, carbon tetrachloride and ethylene chloride; nitro compounds such as nitromethane, nitroethane and nitrobenzene; nitrile compounds such as acetonitrile, propionitrile and benzonitrile; ethers such as diethyl ether, dimethoxyethane and tetrahydrofuran; ketones such as acetone, methyl ethyl ketone and cyclohexanone; carboxylic acids such as acetic acid; esters such as methyl acetate and ethyl acetate; aprotic polar solvents such as dimethylformamide, dimethylacetamide and dimethyl sulfoxide; and mixed solvents of them.

The Ru-Sn hetero-polynuclear complex thus formed and represented by the general formula (2) may be purified by the conventional purification techniques such as recrystallization.

Among the catalysts according to the present invention, a series of compounds represented by the following general formulas (30), (40), (50), (4) or (5), i.e., the Ru-Sn hetero-polynuclear complexes, are also preferable:

ZRu{P(OR$^b$)₃}₂(SnY₃)  (30)

[wherein Z represents a monovalent cyclic dienyl group, Y represents a halogen atom, an alkyl group, a cycloalkyl group, an aryl group, an aralkyl group or an alkoxyl group, and R$^b$ represents an alkyl group, a cycloalkyl group, an aryl group or an aralkyl group], ZRu(dppa)(SnY₃)  (40)

[wherein Z represents a monovalent cyclic dienyl group, Y represents a halogen atom, an alkyl group, a cycloalkyl group, an aryl group, an aralkyl group or an alkoxyl group, and dppa represents a bis(diphenylphosphino)alkane], ZRu(PPh₃)₂(SnY₃)  (50)

[wherein Z represents a monovalent cyclic dienyl group, Y represents a halogen atom, an alkyl group, a cycloalkyl group, an aryl group, an aralkyl group or an alkoxyl group, and Ph represents a phenyl group], ZRu(dppa)(SnY₃)  (4)

[wherein Z represents a monovalent cyclic dienyl group, Y represents a halogen atom, an alkyl group, a cycloalkyl group, an aryl group, an aralkyl group or an alkoxyl group, and dppa represents a bis(diphenylphosphino)alkane, with the proviso that the general formula (4) does not represent CpRu(1,2-dppp)(SnCl₃) {wherein Cp represents a cyclopentadienyl group and 1,2-dppp represents 1,2-bis(diphenylphosphino)propane}], ZRu(PPh₃)₂(SnY₃)  (5)

[wherein Z represents a monovalent cyclic dienyl group, Y represents a halogen atom, an alkyl group, a cycloalkyl group, an aryl group, an aralkyl group or an alkoxyl group, and Ph represents a phenyl group, with the proviso that the general formula (5) does not represent CpRu(PPh₃)₂(SnCl₃) {wherein Cp represents a cyclopentadienyl group and Ph represents a phenyl group}].

The monovalent cyclic dienyl group, halogen atom, alkyl group, cycloalkyl group, aryl group, aralkyl group, 1,2-bis(diphenylphosphino)alkane and the like in the above general formulas (30), (40), (50), (4) and (5) are the same as those in the general formula (10).

Among the compounds represented by the above general formulas (30), (40), (50), (4) and (5), those represented by the above general formulas (30), (40), (50), (4) and (5) wherein Z is a cyclopentadienyl group, and those represented by the above general formulas (30), (40), (50), (4) and (5) wherein Y is a halogen atom, particularly a chlorine atom or a fluorine atom, are preferable.

Particular examples of the compound represented by the above general formula (30) include CpRu{P(OMe)₃}₂(SnF₃) and CpRu{P(OMe)₃}₂(SnCl₃) (wherein Cp represents a cyclopentadienyl group and OMe represents a methoxy group).

Particular examples of the compound represented by the above general formula (40) include CpRu(1,2-dppe)(SnF₃) and CpRu(1,2-dppe)(SnCl₃) (wherein Cp represents a cyclopentadienyl group and 1,2-dppe represents 1,2-bis(diphenylphosphino)ethane).

Particular examples of the compound represented by the above general formula (50) include CpRu(PPh₃)₂(SnF₃) and CpRu(PPh₃)₂(SnCl₃) (wherein Cp represents a cyclopentadienyl group and Ph represents a phenyl group).

The compound represented by the above general formulas (30), (40), (50), (4) or (5) can be produced by, for example, reacting a ruthenium complex represented by the formula CpRu(A)₂Cl (wherein Cp represents a cyclopentadienyl group and A represents P(OR$^b$)₃, ½(dppa) or PPh₃) with a tin compound such as a tin halide and an ammonium halide.

This reaction is conducted in an appropriate solvent at a temperature, for example, from room temperature to the reflux temperature under stirring.

Examples of the solvent to be used in this reaction include the same solvents as those to be used in the production of the compound represented by the general formula (2).

The complex thus formed may be purified by purification techniques such as recrystallization.

The present invention relates a process for producing acetic acid and/or methyl acetate by using at least one compound selected from the group consisting of methanol, methyl formate and formaldehyde as a starting material and effecting a reaction in the presence of the catalyst according to the present invention described above.

In this process for producing acetic acid and/or methyl acetate, it is preferable that the catalyst represented by the above general formula (1) is used as the catalyst represented by the general formula (10) and that the reaction is effected in the presence of the catalyst.

As the catalyst represented by the above general formula (10) which is used in the process for producing acetic acid and/or methyl acetate according to the present invention, those represented by the above general formulas (2), (30), (40) or (50) are preferable and those represented by the above general formulas (2), (30), (4) or (5) are particularly preferable.

Further, the production process according to the present invention is particularly preferably effected in the presence of the catalyst represented by the above general formulas (30), (40), (50), (4) or (5), wherein Z represents a cyclopentadienyl group.

Thus, the Ru-Sn heteronuclear cluster of the present invention can be suitably used as a catalyst for converting, for example, methanol, methyl formate or (para)-formaldehyde into acetic acid or methyl acetate.

It is conceivable that this reaction proceeds as follows:

$$2CH_3OH \rightarrow 2HCHO + 2H_2$$

$$2HCHO \rightarrow HCOOCH_3$$

$$HCOOCH_3 \rightarrow CH_3COOH$$

$$CH_3COOH + CH_3OH \rightarrow CH_3COOCH_3 + H_2O.$$

As these reaction formulas clearly show, the acetic acid thus formed further reacts with the methanol employed as the starting material to thereby give methyl acetate. Therefore, the formation of methyl acetate can be suppressed and acetic acid can be formed at a high efficiency by lowering the ratio of the methanol in the reaction system.

Under some reaction conditions, methyl formate and methylal, which are useful compounds as precursors of acetic acid and methyl acetate, can also be formed from, for example, methanol, methyl formate or (para)formaldehyde. Accordingly, the process of the present invention is usable also as a process for producing methyl formate and/or methylal by appropriately selecting the reaction conditions. It is conceivable that the reaction whereby methylal is formed from methanol and formaldehyde proceeds as follows:

$$HCHO + 2CH_3OH \rightarrow CH_3OCH_2OCH_3 + H_2O.$$

The production process according to the present invention is characterized in that at least one component selected from among methanol, methyl formate and formaldehyde is reacted by using the above-mentioned Ru-Sn hetero-polynuclear complex as a catalyst.

Although the Ru-Sn hetero-polynuclear compound, i.e., the Ru-Sn hetero-polynuclear complex, as such may be subjected to the reaction as a solid catalyst, it is preferable that the compound is supported on a support and then used in order to further elevate the catalytic activity.

Examples of the support include inorganic supports such as activated carbon, silica, alumina, silica-alumina, clay minerals, e.g., zeolite, copper oxide, bentonite, magnesia, silica-magnesia, titania and zirconia; and organic ones such as ion exchange resins and chelating resins. Among these supports, one comprising at least one member selected from the group consisting of inorganic supports such as activated carbon, silica, alumina, zeolite, copper oxide, titania and zirconia; and organic ones such as ion exchange resins and chelating resins are preferable. Preferable examples of the support include those which are resistant to high temperatures exceeding the reaction temperature.

A catalyst supported on a support can be prepared by conventional techniques such as precipitation, impregnation and ion exchange.

The amount of the catalyst to be supported can be selected over a wide range, so long as the efficiency for producing acetic acid and methyl acetate is not lowered thereby. For example, from 0.1 to 200 parts by weight, preferably from 1 to 100 parts by weight and more preferably from 5 to 80 parts by weight, of the catalyst may be used based on 100 parts by weight of the support.

The solid catalyst may be in any form, including powder, granule, pellet, bar, ellipsoid and sphere.

By appropriately combining the kind of the above-mentioned reactant(s), i.e., the starting material, with that of the catalyst, acetic acid, methyl acetate and precursors thereof are efficiently produced.

In the presence of the above-mentioned catalyst, methanol is converted mainly into methyl acetate. In some reaction conditions, precursors of acetic acid such as methyl formate and methylal are formed as by-products. A pentacoordinated complex of the general formula (2), wherein d=3 and $CpRu(PPh_3)_2(SnF_3)$ are particularly effective in the conversion of methanol into methyl acetate.

Further, in the presence of the above-mentioned catalyst, methyl formate is isomerized mainly into acetic acid. However, the acetic acid thus formed is transesterified with methyl formate, which is contained in a large amount, and usually obtained in the form of methyl acetate.

Furthermore, in the presence of the above-mentioned catalyst, formaldehyde is converted into acetic acid and methyl acetate. Similar to the case of methanol, acetic acid precursors such as methyl formate and methylal are formed as by-products in some reaction conditions. The above-mentioned formaldehyde include formaldehyde and paraformaldehyde and, in addition, compounds capable of forming formaldehyde under the employed reaction conditions, for example, trioxane.

As the reactant, i.e., as the starting material, methanol, methyl formate and formaldehyde may be used alone or by mixing two or more of them.

In the production process according to the present invention, wherein at least one member among the above-mentioned components is used as the starting material, the selectivity of the reaction widely varies depending on the reaction conditions, such as the type of the employed catalyst and the reaction temperature. Therefore, acetic acid or methyl acetate can be obtained at a high selectivity by appropriately selecting the reaction conditions.

Further, acetic acid precursors such as methyl formate and methylal formed as by-products can be converted into the target product, i.e., acetic acid or methyl acetate by using two or more catalysts that are different from each other or by appropriately combining the reaction conditions, e.g., the reaction temperature.

Thus, the selectivity for acetic acid or methyl acetate can be improved.

The reaction can be effected by both the liquid phase method and gas phase method. The above-mentioned catalyst is characterized by being soluble in organic solvents, which makes it particularly useful as a homogeneous catalyst in a liquid phase reaction.

In the liquid phase reaction, the reactant, i.e., the starting material, per se or the intermediate may be used as a solvent. Alternately, an inert solvent against the reaction may be employed.

Examples of the solvent to be used in the liquid phase reaction include nitro compounds such as nitromethane, nitroethane and nitrobenzene; nitrile compounds such as acetonitrile, propionitrile and benzonitrile; ethers such as diethyl ether, dimethoxyethane and tetrahydrofuran; ketones such as acetone, methyl ethyl ketone and cyclohexanone; carboxylic acids such as acetic acid; esters such as methyl acetate and ethyl acetate; aprotic polar solvents such as dimethylformamide, dimethylacetamide and dimethyl sulfoxide; halogenated hydrocarbons such as dichloromethane, trichloromethane, carbon tetrachloride and ethylene chloride; aliphatic hydrocarbons such as hexane, heptane and octane; alicyclic hydrocarbons such as cyclohexane; aromatic hydrocarbons such as benzene, toluene and xylene; and mixed solvents thereof.

The catalyst concentration in the reaction liquid, i.e., the mixture comprising the starting material and the solvent, may be appropriately selected depending on the solubility of the complex catalyst and the degree of the catalytic activity thereof. In general, the catalyst concentration ranges from 0.001 to 500 mM, preferably from about 0.01 to 100 mM. Since the Ru-Sn hetero-polynuclear complex to be used in the production process of the present invention has a high solubility in the reactant, i.e., methanol as the starting material and in organic compounds such as acetic acid as the target product, it is possible to elevate the catalyst concentration and, therefore, to elevate the reaction rate in the process according to the present invention.

The liquid phase reaction can be effected at a reaction temperature of, for example, from 0° to 300° C., preferably from about 30° to 200° C. The reaction can be effected in an inert (for example, nitrogen, helium or argon) gas atmosphere under atmospheric or elevated pressure. The reaction may be carried out by both batch and continuous processes. The ratio of the starting component such as methanol per mol of the complex can be appropriately selected, so long as the efficiency for producing acetic acid and methyl acetate is not lowered thereby. It ranges, for example, from 0.1 to 10,000 mol, preferably from about 1 to 1,000 mol.

The dehydrogenation of methanol in the gas phase is effected at a temperature of, for example, from 20° to 400° C., preferably from about 50° to 300° C. The reaction is preferably effected in an inert gas (for example, nitrogen gas, helium gas or argon gas) atmosphere under atmospheric or elevated pressure. The reaction may be carried out by both batch and continuous processes.

When the gas phase reaction is carried out batchwise, the ratio of the methanol to the complex may be appropriately selected, so long as the efficiency for producing acetic acid and methyl acetate is not lowered thereby. The ratio of the starting material per mol of the complex ranges, for example, from 0.1 to 10,000 mol, preferably from about 10 to 1,000 mol.

When the gas phase reaction is continuously carried out, the amount of the starting material to be supplied, based on 1 mol of the complex, may be selected from a wide range wherein the efficiency for producing acetic acid and methyl acetate is not lowered, for example, from a wide range of from 0.001 to 1,000 mol/min, preferably from 0.01 to 100 mol/min.

In the case of a continuous gas phase reaction, each of the conventional processes, for example, a process with the use of a fixed bed or a fluidized bed or a reaction distillation process may be employed.

The catalyst comprising the Ru-Sn hetero-polynuclear complex which is used in the production process of the present invention is highly soluble in organic solvents and has a catalytic ability to convert methanol, methyl formate and formaldehyde into acetic acid and/or methyl acetate. Therefore, the catalyst is useful for producing acetic acid or methyl acetate through a one-stage reaction wherein methanol and the like are used as the starting material(s).

According to the process of the present invention wherein the above-mentioned Ru-Sn hetero-polynuclear complex is used as a catalyst, the catalyst concentration in the reaction system can be elevated and its high catalytic activity can be maintained for a long time. Thus, acetic acid or methyl acetate can be produced from methanol, methyl formate or formaldehyde through a one-stage reaction.

EXAMPLES

Although the present invention will be described with reference to the following Examples in greater detail, it should not be considered that these Examples limit the scope of the present invention.

Example 1 Preparation of $[RuCl(SNCl_3)\{P(OCH_3)_3\}_4]$

All procedures for preparing the title compound were effected in an argon atmosphere.

0.20 g of $[RuCl_2\{P(OCH_3)_3\}_4]$ was dissolved in 5 ml of carbon tetrachloride. After adding 0.35 g of $[(PPh_4)(SnCl_3)]$ thereto, the resultant mixture was heated at 80° C. under stirring for 1 hour.

The mixture was allowed to cool to room temperature and n-hexane was added thereto to precipitate crystals of $[RuCl(SnCl_3)\{P(OCH_3)_3\}_4]$. The yield was 72% on the basis of Ru. The product was purified by recrystallization from methylene chloride/petroleum ether.

| | Elemental analysis (%): | |
|---|---|---|
| | C | H |
| found | 17.15 | 4.61 |
| calculated | 16.79 | 4.21 |

$^{31}P$ NMR chemical shift δ: 127.7 ppm (reference: 85% $H_3PO_4$)

$^{119}Sn$ NMR chemical shift δ: −154.6 ppm (reference: $Sn(CH_3)_4$)

$2J\ (^{31}P-^{119}Sn) = 402$ Hz

Example 2 Conversion of Paraformaldehyde

In an argon atmosphere and at room temperature, 0.0214 g of [RuCl(SnCl$_3$){P(OCH$_3$)$_3$}$_4$] and 0.0375 g of paraformaldehyde were dissolved in 50 ml of nitromethane and the resultant mixture was packed in a glass ampoule. After degassing by evacuation, the glass ampoule was heat-sealed and the contents were allowed to react at 65° C. for 20 hours.

The result of the gas chromatographic analysis on the reaction products indicated that 0.0093 g of methyl formate, 0.0064 g of methylal, 0.0050 g of acetic acid and 0.0013 g of methyl acetate had been formed. The yields (on the basis of formaldehyde) of the products, i.e., methyl formate, methylal, acetic acid and methyl acetate, were respectively 12.4%, 6.7%, 6.7% and 1.4%.

Example 3 Conversion of Methyl Formate

The reaction was effected in the same manner as that of Example 2 except that the paraformaldehyde was replaced by 24.3 g (25 ml) of methyl formate and that the amount of nitromethane was reduced to 25 ml.

As a result, 0.0025 g (yield: 0.0084%) of methyl acetate was formed.

Example 4 Preparation of [Ru(SnCl$_3$)$_2${P(OCH$_3$)$_3$}$_3$]

All procedures for preparing the title compound were effected in an argon atmosphere.

0.76 g of [RuCl$_2${P(OCH$_3$)$_3$}$_4$] was dissolved in 10 ml of methanol. After adding 1.00 g of SnCl$_2$.2H$_2$O thereto, the resultant mixture was heated at 70° C. under stirring for 1 hour.

The mixture was allowed to cool to room temperature and n-hexane was added thereto to precipitate crystals of [Ru(SnCl$_3$)$_2${P(OCH$_3$)$_3$}$_3$]. The yield was 55% on the basis of Ru. The product was purified by recrystallization from nitromethane/methanol.

|  | Elemental analysis (%): | |
|---|---|---|
|  | C | H |
| found | 12.11 | 3.03 |
| calculated | 11.72 | 2.90 |

$^{31}$P NMR chemical shift δ: 132.3 ppm (reference: 85% H$_3$PO$_4$)

$^{119}$Sn NMR chemical shift δ: −85.2 ppm (reference: Sn(CH$_3$)$_4$)

$^2$J ($^{31}$P—$^{119}$Sn)=363 Hz

Example 5 Conversion of Paraformaldehyde

The reaction was effected in the same manner as that of Example 2 except that the [RuCl(SnCl$_3$){P(OCH$_3$)$_3$}$_4$] was replaced by 0.0231 g of [Ru(SnCl$_3$)$_2${P(OCH$_3$)$_3$}$_3$].

As a result, 0.0163 g of methyl formate, 0.0146 g of methylal, 0.0082 g of acetic acid and 0.0029 g of methyl acetate were formed. The yields (on the basis of formaldehyde) of the products, i.e., methyl formate, methylal, acetic acid and methyl acetate, were respectively 21.6%, 15.4%, 10.9% and 3.1%.

Example 6 Conversion of Methyl Formate

The reaction was effected in the same manner as that of Example 3 except that the [RuCl(SnCl$_3$){P(OCH$_3$)$_3$}$_4$] was replaced by 0.0231 g of [Ru(SnCl$_3$)$_2${P(OCH$_3$)$_3$}$_3$].

As a result, 0.0021 g (yield: 0.0070%) of methyl acetate was formed.

Example 7 Conversion of Methanol

The reaction was effected in the same manner as that of Example 6 except that the methyl formate was replaced by 19.8 g of methanol.

As a result, 0.0039 g of methyl acetate, 0.0021 g of methyl formate and 0.0007 g of methylal were formed. The yields of methyl acetate, methyl formate and methylal were respectively 0.0085%, 0.0056% and 0.002%.

Example 8 Conversion of Methanol

The reaction was effected in the same manner as that of Example 7 except that 0.231 g of [Ru(SnCl$_3$)$_2${P(OCH$_3$)$_3$}$_3$], 0.320 g of methanol and 50 ml of nitromethane were used and that the reaction temperature was adjusted to 140° C.

As a result, 0.0222 g of methyl acetate and 0.0288 g of methyl formate were formed. The yields of methyl acetate and methyl formate were respectively 3.0% and 4.8%.

Example 9 Preparation of [CpRu(PPh$_3$)$_2$(SnF$_3$)]

0.50 g of [CpRu(PPh$_3$)$_2$Cl] [see M. I. Bruce et al., Inorg. Synth., 28,270 (1990)], 0.26 g of SnF$_2$ and 1.26 g of NH4F were dissolved in a mixed solvent comprising methanol (50 ml) and pure water (2 ml) and the resultant mixture was heated under reflux for 30 minutes. The resultant mixture was allowed to cool to room temperature. Yellow precipitate was formed. This precipitate was separated by filtration, successively washed with pure water, methanol and ether and dried in a vacuum to thereby give the target compound (0.60 g, yield: 90% on the basis of Ru). This product was recrystallized from dichloromethane/ methanol.

|  | Elemental analysis (%): | |
|---|---|---|
|  | C | H |
| found | 55.80 | 4.23 |
| calculated | 56.04 | 4.07 |

$^{31}$p NMR chemical shift δ: 46.4 ppm (solvent: chloroform, reference: 85% H$_3$PO$_4$)

Example 10 Preparation of [CpRu(1,2-dppe)(SnCl$_3$)]

0.23 g of [CpRu(1,2-dppe)Cl] [see G. S. Ashby et al., Aust. J. Chem., 32, 1003 (1979)]and 0.15 g of SnCl$_2$.2H2O were dissolved in a mixed solvent comprising methanol (120 ml) and benzene (30 ml) and the resultant mixture was heated under reflux for 3 hours. Thus a yellow, homogeneous solution was obtained. After allowing it to cool to room temperature, the solution, was concentrated to 20 ml under a reduced pressure and then a mixture of ether (5 ml) and n-hexane (10 ml) was added thereto. A yellow precipitate was formed. This precipitate was separated by filtration, successively washed with methanol and ether and dried in a vacuum to thereby give the target compound (0.18 g, 60% on the basis of Ru). This product was recrystallized from dichloromethane/methanol.

|  | Elemental analysis (%): | |
|---|---|---|
|  | C | H |
| found | 46.77 | 3.30 |
| calculated | 47.15 | 3.70 |

$^{31}$P NMR chemical shift δ: 76.9 ppm (solvent: chloroform, reference: 85% H$_3$PO$_4$)

Example 11 Preparation of [CpRu{P(OMe)$_3$}$_2$(SnCl$_3$)]

0.23 g of [CpRu{P(OMe)$_3$}$_2$Cl] [see G. S. Ashby et al., Aust. J. Chem., 32, 1003(1979)] and 0.25 g of SnCl$_2$.2H$_2$O were dissolved in 40 ml of methanol and the resultant mixture was heated under reflux for 30 minutes. Since a yellow, homogeneous solution was obtained, this solution was allowed to cool to room temperature, and concentrated to 10 ml under a reduced pressure. Then, a mixture of ether (3 ml) and n-hexane (6 ml) was added thereto. A yellow precipitate was formed. This precipitate was separated by filtration, successively washed with ether and n-hexane and dried in a vacuum to thereby give the target compound (0.29 g, yield: 90% on the basis of Ru). This product was recrystallized from benzene/n-hexane.

| | Elemental analysis (%): | |
| --- | --- | --- |
| | C | H |
| found | 20.33 | 3.47 |
| calculated | 20.66 | 3.63 |

$^{31}$P NMR chemical shift δ: 156.8 ppm (solvent: chloroform, reference: 85% H$_3$PO$_4$)

Example 12

Figure 1:
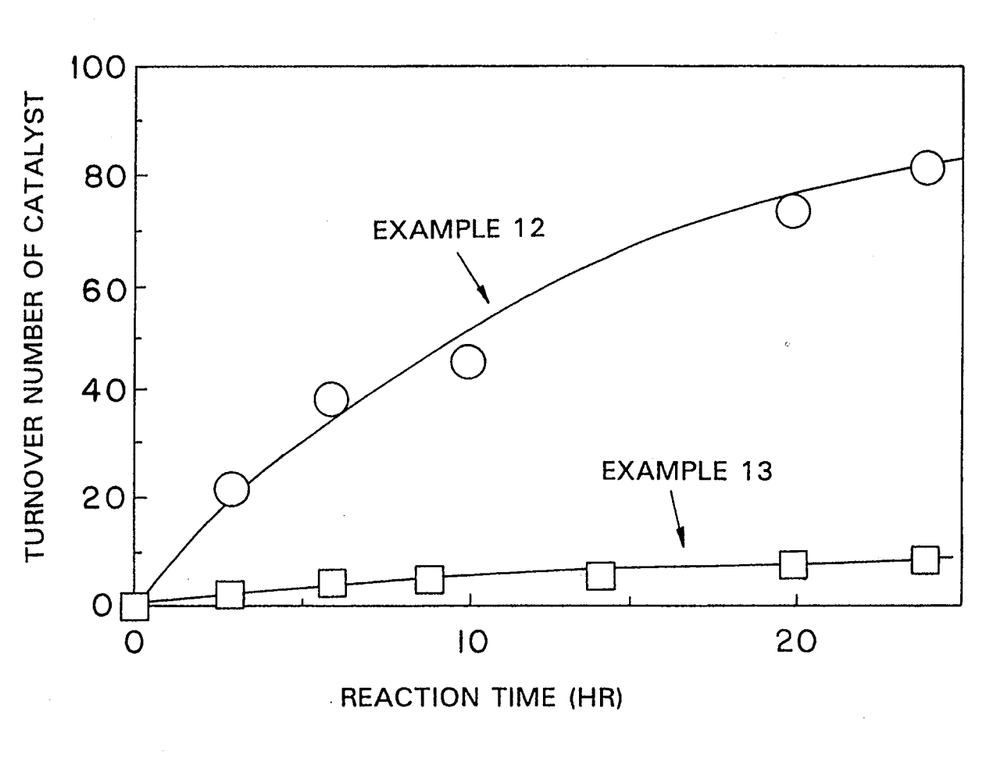
FIG. 1 is a graph showing the relationship between the reaction time and the turnover number of the catalyst in Examples 12 and 13.

3.5 mg (4.0 μmol) of the [CpRu(PPh$_3$)$_2$(SnF$_3$)] obtained in Example 9 and 7.9 g (10 ml) of methanol were dissolved in 10 ml of acetonitrile to thereby give a reaction solution (the concentration of the catalyst being 0.20 mM) A 1-ml portion of this reaction solution was packed in a glass ampoule in an argon atmosphere. After degassing by evacuation, the glass ampoule was heat-sealed and the contents were allowed to react at 120° C. for 24 hours. The result of the gas chromatographic analysis on the reaction product indicated that methyl acetate had been formed at the turnover number of the catalyst of 81, a formation ratio of 0.39% and a selectivity of 100%. The relationship between the reaction time and the turnover number of the catalyst is as described in FIG. 1. The formation ratio and the selectivity of methyl acetate were calculated on the basis of the conversion of methanol.

Example 13

The reaction was effected in the same manner as that of Example 12 except that 3.7 mg (4.0 μmol) of [CpRu(PPh$_3$)$_2$(SnCl$_3$)] [prepared by a method described in T. Blackmore et al., J. Chem. Soc. A, 2376(1971)] was used. As a result, methyl acetate was formed at a turnover number of a catalyst of 8.4, a formation ratio of 0.041% and the selectivity of 100%. The relationship between the reaction time and the turnover number of the catalyst is as described in FIG. 1.

Example 14

The reaction was effected in the same manner as that of Example 12 except that 3.2 mg (4.0 μmol) of [CpRu(1,2-dppe)(SnCl$_3$)] obtained in Example 10 was used. As a result, methyl acetate was formed at a turnover number of the catalyst of 11, a formation ratio of 0.053% and a selectivity of 100%.

Example 15

The reaction was effected in the same manner as that of Example 12 except that 2.6 mg (4.0 μmol) of [CpRu{P(OMe)$_3$}$_2$(SnCl$_3$)] obtained in Example 11 was used. As a result, methyl acetate was formed at a turnover number of the catalyst of 7.5, a formation ratio of 0.036% and the selectivity of 100%.

Comparative Example 1

The reaction was effected in the same manner as that of Example 12 except that 2.9 mg (4.0 μmol) of a complex [CpRu(PPh$_3$)$_2$Cl] having no SnX$_3$$^-$ ligand was used as the catalyst. As a result, methyl acetate was formed at a turnover number of the catalyst of 5.1, a formation ratio of 0.024% and a selectivity of 100%. This catalytic activity was much lower than that observed in Example 12.

I claim:

1. A catalyst represented by the following general formula (10):

$$Ru(SnY_3)_m(L)_n \qquad (10)$$

wherein Y represents a halogen atom, an alkyl group, a cycloalkyl group, an aryl group, an aralkyl group or an alkoxyl group, L represents a ligand, m is an integer of 1 to 6, n is an integer of 0 to 5 and m+n is an integer of 1 to 6.

2. The catalyst as claimed in claim 1, wherein in the general formula (10), m is 1 or 2, n is an integer of 1 to 5 and m+n is 5 or 6.

3. The catalyst as claimed in claim 1 which is represented by the following general formula (1):

$$Ru(SnY_3)_m(L)_n \qquad (1)$$

wherein Y represents a halogen atom, an alkyl group, a cycloalkyl group, an aryl group, an aralkyl group or an alkoxyl group, L represents a ligand, m is an integer of 1 to 6, n is an integer of 0 to 5 and m+n is an integer of 1 to 6, with the proviso that the general formula (1) does not represent CpRu(SnCl$_3$)(L$^a$)$_2$, wherein Cp represents a cyclopentadienyl group and L$^a$ represents PPh$_3$, As(Ph)$_3$ or ½{1,2-bis(diphenylphosphino)propane, wherein Ph represents a phenyl group.

4. The catalyst as claimed in claim 1, wherein in the general formula (10), Y is a halogen atom.

5. The catalyst as claimed in claim 4, wherein in the general formula (10), Y is a fluorine atom.

6. The catalyst as claimed in claim 1, wherein in the general formula (10), L is at least one ligand selected from the group consisting of a halogen atom, a hydrogen atom, a coordinative carbon-containing ligand, a coordinative nitrogen-containing ligand, a coordinative oxygen-containing ligand, a coordinative phosphorus-containing ligand, a coordinative sulfur-containing ligand and a coordinative arsenic-containing ligand.

7. The catalyst as claimed in claim 1, wherein in the general formula (10), L is at least one ligand selected from the group consisting of a halogen atom, a hydrogen atom, a coordinative carbon-containing ligand (other than CO), a coordinative nitrogen-containing ligand, a coordinative oxygen-containing ligand (other than CO), a coordinative phosphorus-containing ligand, a coordinative sulfur-containing ligand and a coordinative arsenic-containing ligand.

8. The catalyst as claimed in claim 1, wherein in the general formula (10), L is at least one ligand selected from the group consisting of a halogen atom, $PR^a{}_3$, wherein $R^a$ represents an alkyl group a cycloalkyl group, an aryl group, an aralkyl group, an alkoxyl group, an aryloxy group or an arylalkoxyl group), $P(OR^b)_3$ wherein $R^b$ represents an alkyl group, a cycloalkyl group, an aryl group or an aralkyl group, ½{bis(diphenylphosphino)alkane} and a monovalent cyclic dienyl group.

9. The catalyst as claimed in claim 1 which is represented by the following general formula (2):

$$RuX_c\{P(OR^b)_3\}_d(SnY^a{}_3)_m \qquad (2)$$

wherein X and $Y^a$ is the same or different from each other and each represents a halogen atom, $R^b$ represents an alkyl group, a cycloalkyl group, an aryl group or an aralkyl group, c is 0 or 1, m is 1 or 2, c+m is 2, d is 3 when c is 0 and d is 4 when c is 1.

10. The catalyst as claimed in claim 1 which is represented by the following general formulas (30), (40) or (50):

$$ZRu\{P(OR^b)_3\}_2(SnY_3) \qquad (30)$$

wherein Z represents a monovalent cyclic dienyl group, Y represents a halogen atom, an alkyl group, a cycloalkyl group, an aryl group, an aralkyl group or an alkoxyl group, and $R^b$ represents an alkyl group, a cycloalkyl group, an aryl group or an aralkyl group, $$ZRu(dppa)(SnY_3) \qquad (40)$$

wherein Z represents a monovalent cyclic dienyl group, Y represents a halogen atom, an alkyl group, a cycloalkyl group, an aryl group, an aralkyl group or an alkoxyl group, and dppa represents a bis(diphenylphosphino)alkane, $$ZRu\{P(Ph)_3\}_2(SnY_3) \qquad (50)$$

wherein Z represents a monovalent cyclic dienyl group, Y represents a halogen atom, an alkyl group, a cycloalkyl group, an aryl group, an aralkyl group or an alkoxyl group, and Ph represents a phenyl group.

11. The catalyst as claimed in claim 10, which is represented by the general formulas (30), (40) or (50) wherein Z is a cyclopentadienyl group.

12. The catalyst as claimed in claim 1 which is represented by the following general formulas (30), (4) or (5):

$$ZRu\{P(OR^b)_3\}_2(SnY_3) \qquad (30)$$

wherein Z represents a monovalent cyclic dienyl group, Y represents a halogen atom, an alkyl group, a cycloalkyl group, an aryl group, an aralkyl group or an alkoxyl group, and $R^b$ represents an alkyl group, a cycloalkyl group, an aryl group or an aralkyl group, $$ZRu(dppa)(SnY_3) \qquad (4)$$

wherein Z represents a monovalent cyclic dienyl group, Y represents a halogen atom, an alkyl group, a cycloalkyl group, an aryl group, an aralkyl group or an alkoxyl group, and dppa represents a bis(diphenylphosphino)alkane, with the proviso that the general formula (4) does not represent CpRu(1,2-dppp)(SnCl$_3$), wherein Cp represents a cyclopentadienyl group and 1,2-dppp represents 1,2-bis(diphenylphosphino)propane, $$ZRu\{P(Ph)_3\}_2(SnY_3) \qquad (5)$$

wherein Z represents a monovalent cyclic dienyl group, Y represents a halogen atom, an alkyl group, a cycloalkyl group, an aryl group, an aralkyl group or an alkoxyl group, and Ph represents a phenyl group, with the proviso that the general formula (5) does not represent CpRu(PPh$_3$)$_2$(SnCl$_3$) wherein Cp represents a cyclopentadienyl group and Ph represents a phenyl group.

13. The catalyst as claimed in claim 12, wherein in the general formulas (30), (4) and (5), Z is a cyclopentadienyl group.

14. A process for producing acetic acid and/or methyl acetate which comprises using at least one compound selected from the group consisting of methanol, methyl formate and formaldehyde as a starting material and effecting a reaction in the presence of a catalyst represented by the following general formula (10):

$$Ru(SnY_3)_m(L)_n \qquad (10)$$

wherein Y represents a halogen atom, an alkyl group, a cycloalkyl group, an aryl group, an aralkyl group or an alkoxyl group, L represents a ligand, m is an integer of 1 to 6, n is an integer of 0 to 5 and m+n is an integer of 1 to 6.

15. The process for producing acetic acid and/or methyl acetate as claimed in claim 14 which comprises effecting the reaction in the presence of a catalyst represented by the general formula (10), wherein m is 1 or 2, n is an integer of 1 to 5 and m+n is 5 or 6.

16. The process for producing acetic acid and/or methyl acetate as claimed in claim 14, wherein the catalyst represented by the general formula (10) is one represented by the following general formula (1):

$$Ru(SnY_3)_m(L)_n \qquad (1)$$

wherein Y represents a halogen atom an alkyl group a cycloalkyl group, an aryl group, an aralkyl group or an alkoxyl group, L represents a ligand, m is an . integer of 1 to 6, n is an integer of 0 to 5 and m+n is an integer of 1 to 6, with the proviso that the general formula (1) does not represent CpRu(SnCl$_3$)(L$^a$)$_2$ wherein Cp represents a cyclopentadienyl group and L$^a$ represents P(Ph)$_3$, As(Ph)$_3$ or ½{1,2-bis(diphenylphosphino)propane}, wherein Ph represents a phenyl group.

17. The process for producing acetic acid and/or methyl acetate as claimed in claim 14, which comprises effecting the reaction in the presence of a catalyst represented by the general formula (10) wherein Y is a halogen atom.

18. The process for producing acetic acid and/or methyl acetate as claimed in claim 17, which comprises effecting the reaction in the presence of a catalyst represented by the general formula (10), wherein Y is a fluorine atom.

19. The process for producing acetic acid and/or methyl acetate as claimed in claim 14, which comprises effecting the reaction in the presence of a catalyst represented by the general formula (10), wherein L is at least one ligand selected from the group consisting of a halogen atom, a hydrogen atom, a coordinative carbon-containing ligand, a coordinative nitrogen-containing ligand, a coordinative oxygen-containing ligand, a coordinative phosphorus-containing ligand, a coordinative sulfur-containing ligand and a coordinative arsenic-containing ligand.

20. The process for producing acetic acid and/or methyl acetate as claimed in claim 14 which comprises effecting the reaction in the presence of a catalyst represented by the general formula (10) wherein L is at least one ligand selected from the group consisting of a halogen atom, a hydrogen atom, a coordinative carbon-containing ligand (other than CO), a coordinative nitrogen-containing ligand, a coordinative oxygen-containing ligand (other than CO), a coordinative phosphorus-containing ligand, a coordinative sulfur-containing ligand and a coordinative arsenic-containing ligand.

21. The process for producing acetic acid and/or methyl acetate as claimed in claim 14 which comprises effecting the reaction in the presence of a catalyst represented by the general formula (10) wherein L is at least one ligand selected from the group consisting of a halogen atom $PR^a{}_3$, (wherein $R^a$ represents an alkyl group, a cycloalkyl group, an aryl group, an aralkyl group, an alkoxyl group, an aryloxy group or an arylalkoxyl group), $P(OR^b)_3$, wherein $R^b$ represents an alkyl group, a cycloalkyl group, an aryl group or an aralkyl group, ½{bis(diphenylphosphino)alkane} and a monovalent cyclic dienyl group.

22. The process for producing acetic acid and/or methyl acetate as claimed in claim.14 wherein the catalyst represented by the general formula (10) is one represented by the following general formula (2):

$$RuX_c\{P(OR^b)_3\}_d(SnY^a{}_3)_m \qquad (2)$$

wherein X and $Y^a$ is the same or different from each other and each represents a halogen atom, $R^b$ represents an alkyl group, a cycloalkyl group, aryl group or an aralkyl group, c is 0 or 1, m is 1 or 2, c+m is 2, d is 3 when c is 0 and d is 4 when c is 1.

23. The process for producing acetic acid and/or methyl acetate as claimed in claim 14 wherein the catalyst represented by the general formula (10) is one represented by the following general formulas (30), (40).or (50):

$$ZRu\{P(OR^b)_3\}_2(SnY_3) \qquad (30)$$

wherein Z represents a monovalent cyclic dienyl group, Y represents a halogen atom, ah alkyl group, a cycloalkyl group, an aryl group, an aralkyl group or an alkoxyl group and $R^b$ represents an alkyl group, a cycloalkyl group, an aryl group or an aralkyl group, $$ZRu(dppa)(SnY_3) \qquad (40)$$

wherein Z represents a monovalent cyclic dienyl group, Y represents a halogen atom, an alkyl group, a cycloalkyl group, an aryl group, an aralkyl group or an alkoxyl group and dppa represents a bis(diphenylphosphino)alkane, $$ZRu(PPh_3)_2(SnY_3) \qquad (50)$$

wherein Z represents a monovalent cyclic dienyl group, Y represents a halogen atom, an alkyl group, a cycloalkyl group, an aryl group, an aralkyl group or an alkoxyl group and Ph represents a phenyl group.

24. The process for producing acetic acid and/or methyl acetate as claimed in claim 23 which comprises effecting the reaction in the presence of a catalyst represented by the general formulas (30), (40) or (50) wherein Z is a cyclopentadienyl group.

25. The process for producing acetic acid and/or methyl acetate as claimed in claim 14 wherein the catalyst represented by the general formula (10) is one represented by the following general formulas (30). (4) or (5):

$$ZRu\{P(OR^b)_3\}_2(SnY_3) \qquad (30)$$

wherein Z represents a monovalent cyclic dienyl group, Y represents a halogen atom, an alkyl group, a cycloalkyl group, an aryl group, an aralkyl group or an alkoxyl group and $R^b$ represents an alkyl group, a cycloalkyl group, an aryl group or an aralkyl group, $$ZRu(dppa)(SnY_3) \qquad (4)$$

wherein Z represents a monovalent cyclic dienyl group, Y represents a halogen atom, an alkyl group, a cycloalkyl group, an aryl group, an aralkyl group or an alkoxyl group and dppa represents a bis(diphenylphosphino)alkane, with the proviso that the general formula (4) does not represent $CpRu(1,2\text{-dppe})(SnCl_3)$ wherein Cp represents a cyclopentadienyl group and 1,2-dppe represents 1,2-bis(diphenylphosphino)ethane, $$ZRu(PPh_3)_2(SnY_3) \qquad (5)$$

wherein Z represents a monovalent cyclic dienyl group, Y represents a halogen atom, an alkyl group, a cycloalkyl group, an aryl group, an aralkyl group or an alkoxyl group and Ph represents a phenyl group, with the proviso that the general formula (5) does not represent $CpRu(PPh_3)_2(SnCl_3)$, wherein Cp represents a cyclopentadienyl group and Ph represents a phenyl group.

26. The process for producing acetic acid and/or methyl acetate as claimed in claim 25 which comprises effecting the reaction in the presence of a catalyst represented by the general formulas (30), (4) or (5) wherein Z is a cyclopentadienyl group.

27. The process for producing acetic acid and/or methyl acetate as claimed in claim 14 wherein the reaction with the use of at least one compound selected from the group consisting of methanol, methyl formate and formaldehyde as a starting material is effected in a liquid phase.

* * * * *

UNITED STATES PATENT AND TRADEMARK OFFICE
CERTIFICATE OF CORRECTION

PATENT NO. : 5,414,110
DATED : May 9, 1995
INVENTOR(S) : Sumio SHINODA

It is certified that error appears in the above-indentified patent and that said Letters Patent is hereby corrected as shown below:

Column 19, line 49; change "ah alkyl" to
---an alkyl---.

Signed and Sealed this

Second Day of January, 1996

*Attest:*

BRUCE LEHMAN

*Attesting Officer*         *Commissioner of Patents and Trademarks*